United States Patent
Comely et al.

(10) Patent No.: US 6,806,389 B1
(45) Date of Patent: Oct. 19, 2004

(54) CATALYST FOR PAUSON-KHAND REACTION

(75) Inventors: Alex Christian Comely, Strand London (GB); Sue Elizabeth Gibson, Strand London (GB); Neil James Hales, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/069,356

(22) PCT Filed: Aug. 21, 2000

(86) PCT No.: PCT/GB00/03192

§ 371 (c)(1),
(2), (4) Date: Apr. 19, 2002

(87) PCT Pub. No.: WO01/16058

PCT Pub. Date: Mar. 8, 2001

(30) Foreign Application Priority Data

Aug. 27, 1999 (GB) .............................................. 9920296

(51) Int. Cl.$^7$ ............................ C07C 45/49; B01J 31/00
(52) U.S. Cl. ...................... 568/342; 568/349; 568/365; 502/152; 502/162
(58) Field of Search ................................ 568/342, 349, 568/365; 502/152, 162

(56) References Cited

U.S. PATENT DOCUMENTS 6,174,840 B1 * 1/2001 Pauson et al.

OTHER PUBLICATIONS

Foster et al. The reactions of free and surface–anchored phosphines with multidentate ligand stabilized metal carbonyl cluster complexes. ☐☐Joural of Organometallic Chemistry (1985), 295 (1) p 99–108.*

Rao et al. Novel Syntheses of Cyclopentenones and Alkenylsilanes from the Corresponding Alkyne–Dicobalt Hexacarbonyl Complexes. Organometallics, 1996 vol. 15 (1) p 442–445.*

Spritzer et al.; "Polymer–supported synthesis as a tool for improving chemoselectivity: Pauson–Khand reaction", TETRAHEDRON, vol. 53, No. 20, 1997, pp. 6791–6808; XP004105664, Oxford GB, Schemes 1 and 2; table 1.

Smit; New route to the synthesis of polycyclic compounds based on a stepwise AdE–reaction of dicobalt octacarbonyl complexes of conjugated enynes with a subsequent intramolecular Khand–Pauson type reaction Tetrahedron Letters, vol. 27, No. 11, 1986, pp. 1241–1244, XP002156524, Oxford GB, p. 1243.

Simonian; "Adsorption effects on the efficiency of cobalt-–mediated cyclizations of allylpropargyl ethers into derivatives 3–oxabicyclo'3.3.0!oct–5–3n–7–one"; Tetrahedron Letters, vol. 27, No. 11, 1986, pp. 1245–1248, XP002156525, Oxford GB, pp. 1246–1247.

Comley; "Polymer–supported cobalt carbonyl complexes as novel solid–phase catalysts of the Pauson–Khand reaction" Journal of the Chemical Society, Chemical Communications, No. 4, Feb. 21, 2000, pp. 305–306, XP002156527, Letchworth GB, whole document.

Comley; "Polymer supported cobalt carbonyl complexes as novel traceless alkyne linkers for solid–phase synthesis"; Journal of the Chemical Society, Chemical Communications, No. 20, Oct. 1999, pp. 2075–2076, XP002156526, Letchworth GB, whole document.

Kim; "Cobalt on mesoporous silica; the first heterogeneous Pauson–Khand catalyst"; Journal of American Chemical Society, vol. 122, No. 7, Feb., 2000, pp. 1550–1551, XP02156528, DC US, whole document.

* cited by examiner

*Primary Examiner*—Samuel Barts
*Assistant Examiner*—Sikarl A. Witherspoon
(74) *Attorney, Agent, or Firm*—Morgan, Lewis & Bockius LLP

(57) ABSTRACT

The invention relates to the use of an immobilized transition metal carbonyl complex as a catalyst in the Pauson-Khand reaction and to processes using such as catalyst.

7 Claims, No Drawings

CATALYST FOR PAUSON-KHAND REACTION

The invention relates to the use of an immobilised transition metal carbonyl complex as a catalyst in the Pauson-Khand reaction and to processes using such a catalyst The reaction between an π-alkynedicobalt hexacarbonyl complex, an alkene, and carbon monoxide to produce a cyclopentenone is generally referred to as the Pauson-Khand reaction (P. L. Pauson, *Tetrahedron*, 1985, 41, 5860) (Scheme 1).

Scheme 1:Pauson-Khand reaction

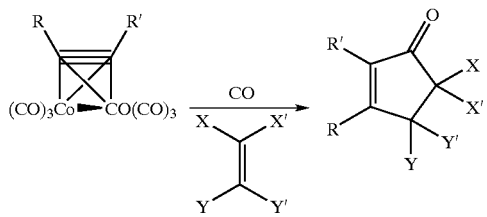

The products of the Pauson-Khand reaction are in general chiral except in the case of certain symmetrical alkenes (X=X' and Y=Y'). If the components of the reaction are racemic or prochiral then chiral cyclopentenones produced by the reaction are produced in racemic form.

The reaction succeeds for a wide range of substrates with the exception of tetrasubstituted alkenes, which are normally unreactive. The stereochemisty (e.g. M. E. Kraft, *J Amer. Chem. Soc.*, 1988, 110, 968) and regiochemistry (e.g. K. H. Dotz and M. Popall, *Teirahedron*, 1985, 41, 5797) of the reaction have been the subject of investigation, for instance in the case of unsymmetrical alkynes the larger substituent (e.g. R') generally forms the substituent at the a carbon of the cyclopentenone. In cases where the alkyne and alkene are both part of the same organic molecule the reaction forms two rings and where the olefin is itself cyclic tricyclic products are easily produced so that the reaction can give products of great complexity.

Accordingly the reaction is valuable because it makes complex organic molecules from simple components and these complex molecules are valuable per se or as intermediates for the production of high value-added products such as pharmaceuticals and fine chemicals.

Mixtures of an alkyne, an alkene, and carbon monoxide can also be converted in situ into π-alkynedicobalt hexacarbonyl complexes using stoichiometric amounts of dicobalt octacarbonyl or its tricobalt or tetracobalt homologues as part of the synthetic route leading to cyclopentenones.

Substoichiometric amounts of dicobalt octacarbonyl or π-alkynedicobalt hexacarbonyl have also been used to catalyse the formation of cyclopentenones from alkynes, alkenes, and carbon monoxide (e.g. I. U. Khand, G. R. Knox, P. L. Pauson, W. E. Watts, and M. I. Foreman, *J. Chem. Soc., Perkin Trans. I*, 1973, 977; D. B. Belanger, D. J. R O'Mahoney and T. Livinghouse, *Tetrahedron Lett.*, 1998, 39, 7637; and D. B. Belanger and T. Livinghouse, *Tetrahedron Lett.*, 1998, 39, 7641).).

Derivatives of π-alknedicobalt hexacarbonyl complexes such as π-alkynedicobaltcarbonylphosphine complexes have been used in the Pauson-Khand reaction (P. Bladon, P. L. Pauson, H. Brunner and R. Eder, *J. Organometal. Chem.*, 1988, 355, 449) and catalysis of the Pauson-Khand reaction using dicobalt octacarbonyl has been performed in the presence of added ligands such as phosphites and phosphines (N. Jeong, S. H. Hwang, Y. Lee and Y. K. Chung, *J. Amer. Chem. Soc.*, 1994, 116, 3159). Heterobimetallic analogues in which a cobalt atom has been replaced by molybdenum are also known (D. T. Rutherford and S. D. R. Christie *Tetrahedron Lett.*, 1998, 39, 9805).

We use the term "Pauson-Khand" reaction to include all reactions between carbon monoxide, alkenes, and alkynes that are promoted by transition metal complexes and that lead to cyclopentenone formation. Specifically, and preferably, by the use of the term "Pauson-Khand" reaction we refer to Scheme 1, wherein Co is cobalt or any other transition metal as described herein, R and R', X and X', Y and Y' may be the same or different and wherein X and R may be joined together, or X and Y together form a ring system.

Although the Pauson-Khand reaction produces useful products it suffers from a number of drawbacks. Dicobaltoctacarbonyl and its analogues are volatile, toxic, and unstable both to loss of carbon monoxide and to aerial oxidation. Accordingly the cobalt carbonyl reagent poses hazards in storage, use, disposal, and product purification. For best results the commercial reagent often requires rigorous purification immediately before use (e.g. "Impure samples of commercial $Co_2(CO)_8$ must be rigorously purified by recrystallisation from degassed HPLC grade hexane or room temperature sublimation at 50 mTorr immediately prior to use". T. Livinghouse, *Tetrahedron Lett*, 1998, 39, 7637). In addition, generally, the cyciopentenone product may retain metal impurities, especially when used stoicheometrically.

We have recently described the use of immobilised transition metal complexes as traceless linkers for unsaturated organic molecules (WO00/007966). A class of immobilised π-alkynedicobalt hexacarbonyl complexes used as disclosed, in which an alkyne is immobilised using its π-alkynedicobalt hexacarbonyl complex as a traceless link, the alkyne or its derivative would can be easily liberated at the end of a sequence of stoichiometric steps.

We have now found that immobilised cobalt carbonyl complexes prepared for use as traceless linkers are members of an advantageous class of catalysts that promote the Pauson-Khand reaction. The invention is illustrated below.

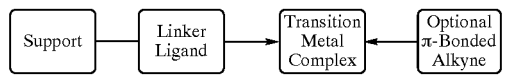

Where the Transition ion Metal Complex is drawn from the group of transition metal-ligand complexes Known to promote the Pauson-Khand reaction and is preferably a cobalt carbonyl or cobalt complex derivative thereof.

For instance, the invention is illustrated below (Catalyst A) where the support is a cross linked polystyrene resin, the linker ligand is a diphenylphosphine, and the transition metal complex is derived from dicobalt octacarbonyl. The representation of Catalyst A is schematic and is not intended to define the chemical constitution or the bonding of the catalytically active species.

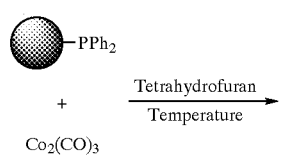

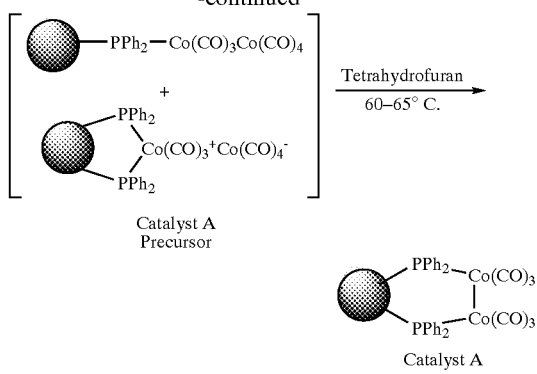

Catalyst A
Precursor

Catalyst A

The method of the invention offers considerable advantages. It is safe and convenient to use at all stages of the operation. The immobilised catalysts may be prepared in active form from commercially available precursors such as dicobalt octacarbonyl (Strem Chemical Co. Inc.) and they retain their activity for longer than their analogues that are not immobilised. The immobilised catalysts are not volatile and are easier to contain than their analogues that are not immobilised. Accordingly they are safer to use, store, and transport. The immobilised catalyst may also be easily recovered from the reaction, for example, by filtration so that valuable catalysts may be recovered for reuse, potential environmental contaminants may be easily eliminated, and the product may be separated from potentially noxious transition metal carbonyl contaminants. Because the catalyst may be easily recovered for reuse the method of the invention enables the economic use of costly transition metal complexes designed to confer special benefits such as the production of enantiomerically pure or enriched cyclopentenones.

An example of the use of an immobilised catalyst is given in Scheme 2.

Presented as a first feature of the invention is the use of an immobilised cobalt carbonyl complex as a catalyst in a Pauson-Khand reaction.

The immobilised π-alkynecobaltcarbonyl complex may also be activated as a catalyst for the Pauson-Khand reaction by prior conversion into an alkyne complex. The alkyne may be one which is the same as the alkyne reagent used in the Pauson-Khand reaction or may be one which is readily displaced by the alkyne reagent used in the Pauson-Khand reaction and therefore will exchange with the alkyne reagent to form a complex with the cobalt.

Presented as a further feature of the invention is the use of an immobilised π-alkynecobalt carbonyl complex as a catalyst for the Pauson-Khand reaction.

A further feature is the use of immobilised analogues and derivatives of cobalt carbonyls and their alkyne complexes as catalysts in a Pauson-Khand reaction.

As discussed above, depending upon the starting alkene starting material, chiral centres may be found in the cyclopentenone product. However, typically, Pauson-Khand reactions produce racemic mires of any product with a chiral centre. In the prior art it is suggested that carbonylmetal complexes can be generated as catalysts for the Pauson-Khand reaction which will produce enatiomerically enriched products. This would be extremely valuable in the pharmaceutical and specialty chemical fields since enatiomerically pure products are desired. However, the drawbacks mentioned above make this prohibitively expensive. In addition any extra effort and expense in producing a complex chiral catalyst would be wasted since little of the original starting catalyst would be available for subsequent reactions. In the present invention the ability to recover a significant amount of catalyst allows increased and rewarding efforts to be made in preparing catalysts for the Pauson-Khand reaction which are able to produce enatiomerically enriched products.

The Pauson-Khand reaction is not limited to complexes of cobalt: other transition metals that are able to form π-alkyne and π-alkene traisitionmetalcarbonyl complexes in the presence of carbon monoxide, alkynes and alkenes are also able to promote cyclopentenone formation from carbon monoxide, alkynes, and alkenes. Such metals form part of the invention described herein and include other metals of the cobalt group, namely rhodium and iridium, from other groups such as; tungsten and molybdenum (T. R. Hoye, J. A. Suriano *Organometallics*, 1992, 11, 2044), titanium (N. M. Kablaoui, F. A. Hicks, and S. L. Buchwald *J. Amer. Chem. Soc.*, 1996, 118, 5818), iron and ruthenium (T. Morimoto, N. Chatani, Y. Fukumoto, and S. Murai, *J. Org. Chem.*, 1997, 62, 3762).

Further features of the invention are the immobilised catalysts, their uses and processes, as defined above or below, in which one [or both] of the cobalt atoms is replaced by a metal independently selected from a transition group metal, preferably of the same periodic group as cobalt. Transition metals that are suitable for use in Pauson-Khand reaction are known to the skilled person or may be tested for their ability to catalyse a Pauson-Khand reaction. Suitable transition metals from the same periodic group as cobalt are selected from; rhodium and iridium; transition metals of other periodic groups include; titanium, ruthenium, tungsten, molybdenum, nickel, and iron.

Immobilised heterobimetallic carbonyl complexes may be formed and these represent a further novel feature of the invention as being particularly useful for producing chiral catalysts of value in the production of enatiomerically enriched cyclopentenone products.

A further feature is the use of a resolved or partially resolved cobalt carbonyl complex wherein one of the cobalt atoms is replaced by different transition metal in a Pauson-Khand reaction to produce, preferably, a resolved or partly resolved product.

A further feature of the invention is a process for the preparation of a cyclopentenone compound or analogues thereof in a Pauson-Khand reaction, which comprises either; reacting an alkyne, an alkene, and carbon monoxide in the presence of an immobilised cobalt carbonyl catalyst; or reacting an alkyne, an alkene, and carbon monoxide in the presence of an immobilised alynecobaltcarbonyl catalyst.

By use of the term "analogues" we mean a compound which is formed by a Pauson-Khand reaction a cyclopentenone ring.

A further feature is the use of resolved or partially resolved complexes in which the cobalt carbonyl complex [e.g. $LCo_2CO_5$alkyne] or a transition metal complex analogues, to prepare a product that is resolved or partially resolved.

The linking group can be any functional group capable of complexing with the transition metal and joining to the support. The linker group is preferably selected from those ligands known to form a strong bond to the transition metal. Suitable ligands include phosphines, phosphites, and isonitriles. Chiral cobalt carbonyl complexes may be prepared by introducing a chiral centre into the linking ligand that connects the support and cobalt.

A further feature is the use of a resolved or partially resolved cobalt carbonyl complex containing a chiral centre within the ligand linking the cobalt to the immobilised support, in a Pauson-Khand reaction to give a product that is, preferably, resolved or partially resolved.

The support to which the catalyst is immobilised may be insoluble, such as a polymer or resin, or soluble, such as a polyethylene glycol (PEG) which can be selectively precipitated as required, or fluorous phases, which show temperature dependent immiscibility with common organic solvents.

In addition the alkyne and alkene reagent for the Pauson-Khand reaction may form part of the same molecule.

The cobalt carbonyl complex may be prepared by one of the following a alternative steps:
(1) bonding the cobalt complex, which has bound to it through a π-complex bond an alkyne, with the support, where either the cobalt complex or support has a linker group capable of forming a bond or interaction between the cobalt complex and the support;
(2) bonding the alkyne with the cobalt complex, which is bound to the support via a linker, by forming a π-complex between the supported cobalt and the alkyne
(3) converting an organic molecule attached to the cobalt metal, which is bound to the support via the linker group, to form a π-complex between the supported cobalt complex and the alkyne.

The invention is illustrated below by the following example where the precursor to the catalytically active species is believed to be polymer-bound dicobalthexacarbonyl, but we do not wish to be limited by this theory.

An example of the use of an immobilised catalyst is given in Scheme 2.

Scheme 2

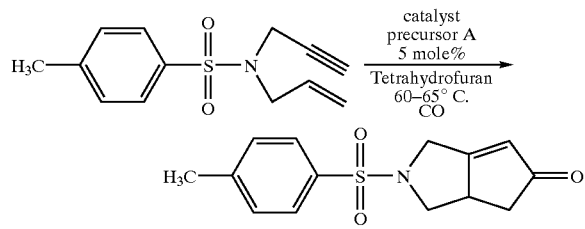

Catalyst A Precursor Resin

Polystyrene-bound diphenylphosphine (2 g, 3.2 mmolP) was suspended at ambient temperature in anhydrous tetrahydrofuran (THF) (15 cm$^3$) and a solution of octacarbonyldicobalt(0) (1.1 g, 3.2 mmol) in anhydrous THF (5 cm$^3$) was added via filter cannula. After 1.5 h under constant nitrogen agitation, the mixture was filtered and the resin was washed with alternate aliquots of THF and diethyl ether until the filtrate became colourless. The resulting deep purple beads were dried in vacuo to afford the resin complex (2.84 g, 1.0 mmol[Co$_2$(CO)$_x$]g$^{-1}$); $v_{max}$(nujol)/cm$^{-1}$ 2074w, 2015msh, 1995ssh, 1979s, 1951m, 1872s; $\delta_p$ (145.8 MHz) (D$_2$O capillary lock) 32 [polymer-P(O)Ph$_2$, 10%], 67 [polymer-(PPh$_2$)$_y$Co$_2$(CO)$_x$, 90%].

EXAMPLES

Example of Catalysis 2,3,3a,4-Tetrahydro-2-[(4-methylphenyl)sulfonyl]-cyclopenta[c]pyrrol-5(1H)-one To a suspension of the catalyst A precursor resin, shown above {24 mg, 0.025 mmol[Co$_2$(CO)$_m$]} in anhydrous THF(5 cm$^3$) was added N-(2-propenyl)-N-(2-propynyl)-4-methylphenylsulfonamide (125 mg, 0.5 mmol) and the resulting mixture was heated to 65° C. under an atmosphere of CO (50 mbar). After 48 h the mixture was filtered, the resin was washed with THF (2×1 cm$^3$) and the combined filtrates were concentrated in vacuo. $^1$H-NMR spectroscopy of the pale yellow residue indicated a 1:1 mixture of starting material and product and no by-products. Purification by flash chromatography (SiO$_2$, 20% EtOAc/hexane) gave the title compound (46 mg, 0.167 mmol, 33%) as a white solid; mp 147–149° C.; $v_{max}$(CH$_2$Cl$_2$)/cm$^{-1}$ 3058, 1716, 1651, 1350, 1164, 1094, 673; $\delta_H$ (360 MHz)(CDCl$_3$) 1.96–2.02 (1 H, m), 2.32 (3 H, s, CH$_3$), 2.48–2.58 (2 H, m), 3.01–3.36 (1 H, m), 3.93–3.98 (2 H, m), 4.27 (1 H, d, J 16.5), 5.92 (1 H, s, C=CH), 7.28 (2 H, d, J 8, Ar-H), 7.66 (2 H, d, J 8, Ar-H); $\delta_C${$^1$H} (90 MHz)(CDCl$_3$) 21.6 (CH$_3$), 39.8 (CH$_2$), 44.0 (CH), 47.7 (CH$_2$), 52.5 (CH$_2$), 126.2 (CH), 127.5 (CH), 130.1 (CH), 133.7 (C), 144.2 (C), 178.6 (C), 207.2 (C=O).

What is claimed is:

1. A process for the preparation of a cyclopentenone ring which comprises reacting carbon monoxide, an alkyne-containing compound and an alkene-containing compound in the presence of a catalyst, where the catalyst comprises:
   a catalytically active component selected from the group consisting of a transition metal-containing carbonyl compound, a π-alkyne-transition metal-containing carbonyl complex and mixtures thereof;
   a support; and
   a linking group connecting the catalytically active component to the support,
wherein the alkyne that is part of the π-alkyne-transition metal-containing carbonyl complex is the same as the alkyne-containing compound or is readily displaced by the alkyne-containing compound.

2. The process of claim 1, wherein two transition metals, which can be the same or different, are present in each catalytically active component.

3. The process of claim 1, wherein the support is a polymer or resin.

4. The process of claim 1, wherein the alkyne-containing compound and the alkene-containing compound are separate compounds.

5. The process of claim 1, wherein the alkyne-containing compound and the alkene-containing compound are the same compound.

6. The process of claim 1, or claim 2, wherein each transition metal present in the catalytically active component is independently selected from the group consisting of cobalt, rhodium, iridium, tungsten, molybdenum, titanium, nickel, iron and ruthenium.

7. The process of claim 6, wherein each transition metal is cobolt.

* * * * *